United States Patent [19]

Cavazza

[11] Patent Number: 5,043,355
[45] Date of Patent: Aug. 27, 1991

[54] USE OF L-CARNITINE DERIVATIVES IN THE THERAPEUTICAL TREATMENT OF PERIPHERAL NEUROPATHIES

[75] Inventor: Claudio Cavazza, Rome, Italy

[73] Assignee: Sigma-Tau Industrie Farmaceutiche Riunite S.p.A., Rome, Italy

[21] Appl. No.: 451,253

[22] Filed: Dec. 15, 1989

[30] Foreign Application Priority Data

Dec. 27, 1988 [IT] Italy .................. 48717 A/88

[51] Int. Cl.$^5$ ............................ A61K 31/225
[52] U.S. Cl. .................... 514/547; 514/903
[58] Field of Search ............ 514/547, 903, 879

[56] References Cited

U.S. PATENT DOCUMENTS

| | | | |
|---|---|---|---|
| 4,343,816 | 8/1982 | Cavazza | 514/554 |
| 4,346,107 | 8/1982 | Cavazza et al. | 514/547 |
| 4,439,438 | 5/1984 | Cavazza | 514/357 |
| 4,751,242 | 6/1988 | Calvani et al. | 514/554 |

FOREIGN PATENT DOCUMENTS 0207011 12/1986 European Pat. Off.

OTHER PUBLICATIONS

Francia; Giorgio, Chem Abstracts 106:32722K (1986).
Benzi; G. et al., Chem Abstracts 98:213670D (1983).
Fariello; R. G. et al., Chem Abstracts 105:127432J (1986).
Chemio Syntex, Chem. Abstracts 107:198929C (1987).

*Primary Examiner*—Richard L. Raymond
*Assistant Examiner*—Gary E. Hollinden
*Attorney, Agent, or Firm*—Oblon, Spivak, McClelland, Maier & Neustadt

[57] ABSTRACT

The use is disclosed of compounds of general formula

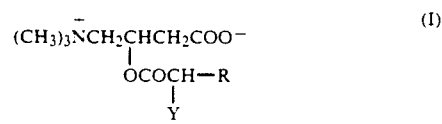

wherein:
Y is methyl, and
R is an unsubstituted or substituted alkyl group selected from methyl, or ethyl, and the pharmacologically acceptable salts thereof, for treating peripheral neuropathies.

The compounds can be administered orally or parenterally.

3 Claims, No Drawings

USE OF L-CARNITINE DERIVATIVES IN THE THERAPEUTICAL TREATMENT OF PERIPHERAL NEUROPATHIES

BACKGROUND OF THE INVENTION

Field of Invention

The present invention relates to the use of acyl derivatives of L-carnitine of formula (I)

$$(CH_3)_3\overset{+}{N}CH_2CHCH_2COO^- \atop \underset{Y}{\underset{|}{OCOCH-R}}} \quad (I)$$

wherein:

Y is hydrogen, methyl or amino, and
R is an unsubstituted or substituted alkyl group selected from methyl, ethyl, 1-methylpropyl, isobutyl, isopropyl, mercaptomethyl and 3-guanidinopropyl, and their pharmacologically acceptable salts for treating degenerative alterations of the nervous system.

Examples of compounds encompassed by formula (I) are the following:

L-isoleucyl L-carnitine: (CH$_3$)$_3\overset{+}{N}$CH$_2$CHCH$_2$COO$^-$ (a)
$\qquad$ |
$\qquad$ OCOCHCHCH$_2$CH$_3$
$\qquad\qquad\qquad$ |
$\qquad\qquad\qquad$ CH$_3$
$\qquad$ |
$\qquad$ NH$_2$ L-leucyl L-carnitine: (CH$_3$)$_3\overset{+}{N}$CH$_2$CHCH$_2$COO$^-$ (b)
$\qquad$ |
$\qquad$ OCOCH$_2$CH(CH$_3$)$_2$
$\qquad$ |
$\qquad$ NH$_2$ L-valyl L-carnitine: (CH$_3$)$_3\overset{+}{N}$CH$_2$CHCH$_2$COO$^-$ (c)
$\qquad$ |
$\qquad$ OCOCH(CH$_3$)$_2$
$\qquad$ |
$\qquad$ NH$_2$ L-cysteinyl L-carnitine: (CH$_3$)$_3\overset{+}{N}$CH$_2$CHCH$_2$COO$^-$ (d)
$\qquad$ |
$\qquad$ OCOCH$_2$SH
$\qquad$ |
$\qquad$ NH$_2$ L-arginyl L-carnitine: (CH$_3$)$_3\overset{+}{N}$CH$_2$CHCH$_2$COO$^-$ (e)
$\qquad$ |$\qquad\qquad\qquad$ NH
$\qquad$ |$\qquad\qquad\qquad$ ||
$\qquad$ OCOCH(CH$_2$)$_3$NHCNH$_2$
$\qquad$ |
$\qquad$ NH$_2$ isovaleryl L-carnitine: (CH$_3$)$_3\overset{+}{N}$CH$_2$CHCH$_2$COO$^-$ (f)
$\qquad$ |
$\qquad$ OCOCH$_2$CHCH$_3$
$\qquad\qquad\qquad$ |
$\qquad\qquad\qquad$ CH$_3$ isobutyryl L-carnitine: (CH$_3$)$_3\overset{+}{N}$CH$_2$CHCH$_2$COO$^-$ (g)
$\qquad$ |
$\qquad$ OCOCHCH$_3$
$\qquad$ |
$\qquad$ CH$_3$ alpha-methylbutyryl L-carnitine: (CH$_3$)$_3\overset{+}{N}$CH$_2$CHCH$_2$COO$^-$ (h)
$\qquad$ |
$\qquad$ OCOCHCH$_2$CH$_3$
$\qquad$ |
$\qquad$ CH$_3$ Formula (I) represents the compounds of the present invention as inner salts.

The compounds of the present invention also encompass the pharmacologically acceptable salts of the compounds of formula (I) that have formula (I')

$$(CH_3)_3\overset{+}{N}CH_2CHCH_2COOH \atop X^- \; \underset{Y}{\underset{|}{OCOCH-R}}} \quad (I')$$

wherein X$^-$ is the anion of a pharmacologically acceptable acid selected from chloride, bromide, orotate, acid aspartate, acid citrate, acid phosphate, acid fumarate, lactate, acid maleate, acid oxalate and acid sulphate. If Y is amino, the pharmacologically acceptable salts of the compounds of formula (I) have general formula (I")

$$(CH_3)_3\overset{+}{N}CH_2CHCH_2COOH \atop X^- \; \underset{\overset{+}{N}H_3X^-}{\underset{|}{OCOCH-R}}} \quad (I'')$$

wherein X$^-$ has the previously indicated meaning.

For the sake of simplicity, reference shall be made hereinbelow to the inner salts of formula (I). However, it should be understood that every disclosure equally applies to the pharmacologically acceptable salts of formula (I') and (I").

DISCUSSION OF THE BACKGROUND

The compounds of formula (I) are known compounds. Thus, for instance, the amino acylcarnitines (a)-(e) and processes for their preparation are disclosed in the European patent application 87830245.4 (publication no. 0252030). These compounds are useful as hepatoprotecting agents.

Isovaleryl L-carnitine is a natural product: it forms by catabolic conversion of L-leucine, one of the essential aminoacids.

No previous therapeutical applications of isovaleryl L-carnitine are known.

Isovaleryl L-carnitine can be synthesized by reacting a solution of L-carnitine chloride in trifluoroacetic acid with isovaleryl chloride at room temperature. Upon termination of the reaction, isovaleryl L-carnitine is precipitated by adding ethyl ether to the reaction mixture (m.p. 173°–175° C.; rotatory optical power —23 (c=1, H$_2$O)).

Also isobutyryl carnitine and alpha-methylbutyryl carnitine are natural products (see e.g. L. L. Bieber e Y. R. Choi, Isolation and identification of aliphatic short-chain acylcarnitines from beef heart: Possible role for carnitine in branched-chain aminoacid metabolism, in Proc. Natl. Acad. Sci USA, 74, n. 7, pp 2795-2798, 1977). Methods for synthesizing these acyl derivatives of carnitine are e.g. disclosed by E. Strack and D. Müller, Darstellung von O-acyl-carnitinen, in Hoppe-Seyler's Z. Physiol. Chem. 351, pp 95-98, 1970 and by T. Bohmer e J. Bremer, Propionylcarnitine, physiological variations in vivo, in Biochim. Biophys. Acta, 152, pp 559-567, 1968. For these compounds, too, no previous therapeutical applications are known.

The use of an acyl derivative of carnitine, viz. acetyl L-carnitine, for treating a particular class of degenerative alterations of the nervous system, i.e. peripheral neuropathies, has been disclosed already (U.S. Pat. No. 4,751,242; European patent application 87830298.3, publication n. 0256999) wherein the definition of peripheral neuropathies is applied to a group of persistent disturbances of the motor neurons of the brain stem and spinal cord and/or the primary sensory neurons and/or the peripheral autonomic neurons, with involvement of the peripheral axons and their attendant supporting structures.

SUMMARY OF THE INVENTION

It has been now surprisingly found that use of the acyl L-carnitine (I) and the pharmacologically acceptable salts thereof (I') and (I'') is effective in the therapeutical treatment of the degenerative alterations of the nervous system. More specifically, according to the present invention the definition of degenerative alterations of the nervous system is applied to atrophy and cerebral degeneration (as for instance occur both in normal aging and in pathological conditions such as Alzheimer's disease, pre-senile and senile dementia, Creutzfeldt-Jakob disease, Huntington's chorea), demyelinating diseases such as multiple sclerosis and pathological degeneration of Purkinje cells and cholinergic neurons of Meynert nucleus.

DESCRIPTION OF THE PREFERRED EMBODIMENTS

The present invention provides, therefore, for a therapeutical method for treating neuronal degenerations which comprises orally or parenterally administering to a patient in need thereof an effective amount of an acyl L-carnitine (I) or the pharmacologically acceptable salts thereof (I') and (I''). In practice, from about 1000 to 2000 mg/day of an acyl L-carnitine (I) or an equivalent amount of a pharmacologically acceptable salt thereof (I') and (I'') are administered orally or parenterally. The treatment generally lasts for at least 30 to 60 days and can be prolonged several months. As compound of formula (I), isovaleryl L-carnitine is particularly preferred.

It is apparent that the pharmaceutical compositions that are most suitable having regard to the therapeutical application of the present invention are compositions that, in unit dosage form, comprise from about 500 to about 1000 mg of acyl L-carnitine of formula (I) or an equivalent amount of a pharmacologically acceptable salt thereof of formula (I') or (I'') and a pharmacologically acceptable excipient therefor.

Examples of suitable compositions in unit dosage forms are for instance disclosed in the U.S. Pat. No. 4,464,393.

It will suffice to substitute one of the compounds of the present invention for acetyl carnitine in the compositions of the above-identified patent.

The efficacy of the compounds (I), (I') and (I'') in the treatment of the degenerative alterations of the nervous system was assessed by both pharmacological tests in experimental animals models and in clinical trials.

Hereinbelow, some of these experiments are illustrated.

PHARMACOLOGICAL TESTS

CLINICAL EVALUATION OF FUNCTIONAL RESTORATION FOLLOWING CUTTING AND IMMEDIATE MICROSURGICAL RECONSTRUCTION OF THE SCIATIC NERVE IN RATS.

In this test male Wistar rats weighing 200-250 grams were used. Following general anesthesia (Nembutal, 4 mg/100 g e.p.) the sciatic nerve was aseptically isolated at the thigh bilaterally. The nerve was incised just distally to the branch to the gluteus maximus and immediately reconstructed via microsurgical peri-perineural anastomosis. Following surgery the rats were randomly subdivided into six groups and subcutaneously injected according to the following scheme:

| Experimental group | Number of rats | Medicament | Dose/day |
|---|---|---|---|
| I | 5 | Saline | 0.2 ml |
| II | 5 | L-carnitine | 50 mg/kg |
| III | 5 | Acetyl L-carnitine | 50 mg/kg |
| IV | 5 | Gangliosides· | 50 mg/kg |
| V | 5 | Isovaleryl L-carnitine | 50 mg/kg |
| VI | 5 | Alpha methylbutyryl L-carnitine | 50 mg/kg |

The treatment began on the first day one minute following surgery and was continued for eight weeks. After this time period, the degree of functional restoration was evaluated according to the following scale proposed by Richardson et al, "Percussive injury to peripheral nerve in rats", J. Neurosurg. 51, 178-187 (1979), and Zalewsk et al, "An evaluation of nerve repair with nerve allografts in normal and immunologically tolerant rats", J. Neurosurg. 52, 557-563 (1980):

0 atrophy of the anterior tibial muscle (AT) and toe long extensor (TLE), foot drop
 1 No atrophy of AT and TLE, foot drop
 2 No atrophy of AT and TLE, no foot drop
 3 No atrophy of AT and TLE, restoration of foot dorsal flexion
 4 No atrophy of AT and TLE, spreading out of toes.

RESULTS

The degree of functional restoration is reported in the following table:

| Experimental group | Clinical rating |
|---|---|
| I | 2.2 ± 1.0 |
| II | 2.8 ± 1.1 |
| III | 3.3 ± 0.7 |
| IV | 1.1 ± 1.1 |
| V | 6.8 ± 0.5 |
| VI | 4.9 ± 0.6 |

The clinical rating is significantly higher in the rats of groups V and VI treated with isovaleryl L-carnitine and alpha methylbutyryl L-carnitine than in the placebo-treated controls ($P \leq 0.05$).

What is claimed is:

1. A method for treating a patient with a peripheral neuropathy, comprising:
   orally or parenterally administering to said patient an effective amount of a composition comprising an acyl L-carnitine selected from the group consisting of isovaleryl L-carnitine and α-methylbutyryl L-carnitine or an equivalent amount of a pharmaceutically acceptable salt thereof and a pharmaceutically acceptable carrier.

2. The method of claim 1, wherein the effective amount of said carnitine compound ranges from 1,000–2,000 mg daily.

3. The method of claim 2, wherein the stated amount of said carnitine compound is administered over a 30–60 day period.

* * * * *